US00PP32754P2

(12) United States Plant Patent
Khayat

(10) Patent No.: US PP32,754 P2
(45) Date of Patent: Jan. 19, 2021

(54) BANANA PLANT NAMED 'ADI 9107'

(50) Latin Name: ***Musa acuminata* (AAA)**
Varietal Denomination: ADI 9107

(71) Applicant: Eli Khayat, Nahariya (IL)

(72) Inventor: Eli Khayat, Nahariya (IL)

(73) Assignee: RAHAN MERISTEM (1998) LTD, Western Gallilee (IL)

( * ) Notice: Subject to any disclaimer, the term of this patent is extended or adjusted under 35 U.S.C. 154(b) by 0 days.

(21) Appl. No.: 16/602,985

(22) Filed: Jan. 9, 2020

(51) Int. Cl.
*A01H 5/08* (2018.01)

(52) U.S. Cl.
USPC ..... Plt./160

(58) Field of Classification Search
USPC ..... Plt./160
See application file for complete search history.

(56) References Cited

U.S. PATENT DOCUMENTS

PP20,645 P3 1/2010 Khayat
2009/0222959 P1 9/2009 Khayat

OTHER PUBLICATIONS

Bennetzen J.L. and Kellogg E.A. (Sep. 1997). Do Plants Have a One-Way Ticket to Genomic Obesity?, in: The Plant Cell, American Society of Plant Botanists, Letters to the Editor, pp. 1509-1514.

Khayat E. and Ortiz R. (2011). Genetics of important traits in Musa, in: Michael Pillay and Abdou Tenkouano (eds): "Banana breeding: constraints and progress", CRC Press pp. 71-84.

Citation: E. Khayat (2018). TR4 Resistant GAL, presented at the International Congress of Plant Pathology, proceedings of the Banana workshop, Jul. 29-Aug. 3, 2018.

Paszkowski J. (Jan. 2015). Controlled activation of retrotransposition for plant breeding, ScienceDirect Current Opinion in Biotechnology 2015, 32:200-206.

Hirochika H., Okamoto H., and Kakutani T. Silencing of Retrotranposons in Arabidopsis and Reactivation by the ddm1 Mutation, The Plant Cell, vol. 12, 357-368, Mar. 2000.

*Primary Examiner* — Annette H Para
(74) *Attorney, Agent, or Firm* — Lyn R Marantz; KK Patents LLC

(57) ABSTRACT

'ADI 9107' is a selection of the ancestral banana line 'ADI', which belongs to *Musa acuminata* cv. Cavendish. When compared to its ancestral line, 'ADI 9107' shows the following characteristics:
No deformation of the upper hands of the fruit bunch,
Dwarf-like stature,
Wider girth size,
Higher fruit yield,
Longer fruit size ("fingers").
Lower number of suckers
Similar pseudostem diameter
Longer petiole length
Shorter peduncle length
Smaller peduncle diameter
Similar length of the bunch
Larger diameter of the bunch
No statistical difference for number of fruit per hand

9 Drawing Sheets

1

'ADI 9107' is a short triploid banana plant belonging to the Cavendish group *Musa acuminata* (AAA). The 'ADI 9107' variety is a mutant of the earlier cultivar named 'ADI' (U.S. Plant Pat. No. 20,645), which was a selection of 'Zelig' originating in the Western Galilee, Israel. The 'Zelig' selection is known as a very unstable selection especially when propagated by tissue culture. The height of the 'Zelig' averages 3.5 meters. In contrast to 'Zelig' the original 'ADI' has a very short stature characteristic (2.15 meters). Despite the high productivity and low stature of the original 'ADI', the variety was not widely accepted in the Caribbean and Central and South America, mainly due to the high incidence of deformation of the upper hand when grown in tropical areas. In some cases, the top two hands are deformed. Consequently, the inventor had to modify the original 'ADI' (Khayat E. U.S. Plant Pat. No. 20,345) to make it more acceptable for the environmental conditions of the Caribbean and Central America. This was achieved via in vitro mutagenesis that induces transcriptional activation of retrotransposable elements. In an earlier report (Khayat and Ortiz, 2011) we have demonstrated that de-methylation of DNA activates retro-transposable elements.

2

An extensive process of tissue culture combined with inclusion of the de-methylation compound 5-Aza-2'-deoxycytidine (AZA) created a large and diverse population of mutants including the 'ADI 9107'. The retro-transposing element expression was used as a marker in the selection process. The 'ADI 9107' was selected on the basis of its short plant stature, high bunch weight, perfect orientation of the upper hands (no visible deformation in the upper hands of the bunch), quick cycling and a high index of productivity.

'ADI 9107' was created using the tissue culture technology as specified below.

i. A meristem was harvested from an 'ADI' shoot that reached the height of 45 cm from the ground level. The meristem was disinfected by immersion in 0.3% commercial sodium hypochlorite solution for 30 minutes, followed by several rinses with sterile distilled water. The disinfection process was repeated 3× as above and subsequently the meristems (0.5×0.5 cm) were placed on a solid medium containing MS salts, 3% w/v sucrose, 10 $mg \cdot L^{-1}$ benzyladenine, and MS vitamins (multiplication medium).

ii. The meristems were incubated for 5 weeks at 22° Celsius under florescent lighting at a regime of 16/8 dark/light hours. The meristems were each subdivided longitudinally into 3 sub-meristems that were each cultured separately. Each of the 20 sub-meristems was incubated for an additional 4 weeks as per the above described environmental conditions.

iii. In subcultures 14 and 18 the medium contained 6.85 mg/L of 5-Aza-2'-deoxycytidine (AZA). The rest of the components in the medium of subcultures 14 and 18 were the same as described above.

iv. In subcultures 8, 12 and 16 we included in the medium 0.1 mg/L of TDZ (Thidiazuron).

v. Following 24 subcultures as indicated in step ii, the meristems were transferred to a medium that contained MS salts, 0.1 $mg \cdot L^{-1}$ kinetin, MS vitamins, and 0.1 $mg \cdot L^{-1}$ 1-naphthaleneacetic acid (NAA) (rooting and regeneration medium).

vi. After 4 weeks of culture in the rooting and regeneration medium, under the environmental conditions indicated in step ii, the plants were individually placed in 10 $cm^3$ peat moss plugs in a greenhouse under mist irrigation. After an additional 4 weeks of growth, each plant was placed in a 5 L pot and permitted to grow until it reached the height of about 60 cm.

vii. At 60 cm in height, the plants were removed from the pots and planted in the field in Kibbutz Rosh Hanikra Western Galilee, Israel, at a density of approximately 1200 plants per 1000 $m^2$.

viii. One single plant, which was named 'ADI 9107' was selected from a population of 5,000 clones times 2 (2 siblings per clone—a total of 10,000 plants) produced as described above in [002] step i.

ix. Following the multiplication of the 'ADI' population of mutants, each clone was assigned an ID number, 1 sibling was sent for selection in Martinique (French Antilles) and the second sibling was planted in a field in the Western Galilee of Israel.

x. Following a double selection in Israel and Martinique, 22 best clones were picked based on their short plant stature, high bunch weight, no visible deformation in the upper hands of the bunch, quick cycling and a high index of productivity (data presented in FIGS. 1-7).

xi. By comparing the data collected in the Western Galilee to those collected in Martinique, 2 best clones were chosen having the best indexing scores in both locations. Among the selected 22 clones the two that scored the highest were the 'ADI 9107' (a shorter clone) and 'ADI 9001'(a taller clone).

xii. Twenty (20) initials from each of the 2 clones were harvested from the field in the Western Galilee and propagated by tissue culture.

xiii. Following 4 cycles of tissue culture as indicated above without the TDZ and AZA, a population of 1500 plants was produced from each of the 2 clones.

xiv. In addition, 1500 plants were produced in the same manner from the cultivar 'GAL', 'JAFFA', and 'GRAND NAIN' and the original ADI (for some parameters) for comparison.

xv. A clonal comparison of the 5 cultivars ('GAL', 'JAFFA', 'GRAND NAINE', 'ADI 9107' and 'ADI 9001') was performed in the Western Galilee. For some parameters also the original 'ADI' was compared. The plants were grown according to normal cultural practices of banana growers in the Western Galilee. A comparison between the different plant lines is exhibited in FIGS. 1-7.

xvi. The selected cultivar did not exhibit malformation while the incident of malformed bunches in the upper two hands in the original 'ADI' was approximately 60% (FIG. 1).

xvii. The selected cultivar 9107 was slightly taller than the original 'ADI' (235 and 220 cm respectively) from the ground level to the highest point in the fruit bunch petiole, while the taller cultivar (9001) is 51 cm taller than the original 'ADI'. A comparison between short (9107) and tall (9001) is exhibited in FIGS. 2 and 3.

xviii. Cycling time did not differ very much between the different 'ADI' cultivars under Israeli conditions, but they all flowered earlier than 'GAL', 'Grand Nain' (GN) and especially 'JAFFA' (FIG. 4). The clone 9107 exhibited longer and heavier fingers than the 9001. Both new 'ADI' cultivars had 2 more fingers in the second hand from the top compared to the other Cavendish cultivars (FIG. 5). The representative finger in 'JAFFA' was heavier than the 'ADI' cultivars and the other Cavendish cultivars. Bunch weights (FIG. 6) of the two 'ADI' cultivars exceeded 'GAL' and 'GN' but not 'JAFFA'. However, when the two components of yield were combined in the indexing formula (FIG. 7) the 9107 received by far the best score (139) compared to 'ADI' (118) and 9001 (125). The rest of the Cavendish cultivars received a lower indexing score.

xix. The new cultivar (9107) benefits from no fruit bunch malformation and received the highest indexing score of the combined components of yield (a combination of short cycling time and high bunch weight).

BACKGROUND OF THE INVENTION

Banana and plantains (*Musa* spp.) comprise major food sources for more than 400 million people worldwide (i). Of the huge volume of fruit production approximately 15% is exported to remote markets. Most banana and plantains are inter or intra hybrids between two species namely *Musa acuminata* (A genome) and *Musa balbisiana* (B genome). By far, the most important export variety is Cavendish (a triploid AAA). In the 1950's, this variety replaced 'Gros Michel' (not patented) which was almost wiped out due to attacks from a new race of the fungal disease, *Fusarium* Wilt Race 1. Being resistant to the disease combined with wide consumer acceptance in export markets made 'Cavendish' irreplaceable. However, due to double sterility and the triploid nature of 'Cavendish', breeders have very limited tools to improve the germplasm of this variety. Consequently, 'Cavendish' bananas suffer from a variety of pests and diseases. In addition, the plants are wind sensitive, have a relatively high stature, short shelf life of the fruit and low tolerance to environmental stresses like lack of or excess water, low mineral nutrition, soil compaction and salinity. Due to the inability of 'Cavendish' to cross hybridize there are very limited sources of variability.

Originally 'ADI' (*Musa acuminata* AAA Cavendish) was a mutant derived from 'Zelig', which is a selection of the cultivar 'Grand Naine'. All 'ADI' cultivars were selected in the Western Galilee, Israel. The ADI mutant has many beneficial agro-technical traits but the most noticeable are low stature and large fruit bunch. The cv. gained some popularity in Martinique and Guadeloupe owing to the ability of growers to spray the canopy against black sigatoka disease from the ground in light of the ban of use air sprays. However, local environmental conditions in the Caribbean Islands and Central America required a modulation of the cv., especially in relation to its extreme low stature and deformation of the upper hand of the fruit bunch. In the present development we describe a new generation of 'ADI' that was selected under the specific environmental conditions of Martinique. The method we have used entails a concomitant evaluation of a mutated population of 'ADI' in two locations, Martinique and Israel. The selected clones were compared to various Cavendish cvs. In many parameters, the new 'ADI' (9107) was superior to competing clones and showed no deformation under the conditions of both locations, in Israel and in Martinique.

In this work we have used a new method of mutagenesis that entails de-methylation of DNA in the in-vitro meristematic culture. This method was proven effective in activation of retro-transposable elements that induce stable mutations in plants (Paczkowski, 2015). Cytosine methylation has been associated with genetic inactivity and a heterochromatic state in many higher eukaryotes, including plants where de novo methylation was first detected during the inactivation of DNA transposable elements of the mutation compound (Bennetzen J. L. et al, 1997). This cytosine methylation has been associated with both transcriptional inactivity and a higher rate of C to T transitions, giving rise to enhanced transcriptional and mutational silencing. The first evidence on the role of DNA methylation in the regulation of retro transposition comes from a study on Ttol by Hirochika et al., (2000). It was observed that after the initial active retro-transposition in the *Arabidopsis* genome, Ttol became silent. In this breeding program we have used the de-methylation compound 5-Aza-2'-deoxycytidine in order to induce mutagenesis in the 'ADI' genome.

This new selection of dessert banana plant was asexually reproduced by corms in tissue culture by the inventor in Rosh Hanikra, Israel. 'ADI 9107' has been proven stable in the field for at least three consecutive generations.

BRIEF DESCRIPTION OF THE FIGURES

FIG. 1 shows photographs that highlight bunch structure comparison of precursor 'ADI' (panel A) and 'ADI 9107' (panel B) in the field in the Western Galilee, Israel. The red circle highlights the malformation in the precursor cultivar 'ADI' in panel A while the bunch in panel B represents 'ADI 9107' with a normal arrangement of the fingers in all hands.

FIG. 2 shows the main morphological characteristic of all the ADI types of its low stature compared to other cultivars of Cavendish. In FIG. 2 we compare the height of the different cvs. The data represent the average of 1500 clones of each of 9001 (tall genotype) and 9107 (short genotype), the precursor 'ADI', 'GAL', 'Grand Naine' ('GN'), and 'JAFFA'. The plants were grown in the Western Galilee, Israel. Measurements were taken in cm ±SD, two weeks after flower appearance of the second fruit cycle ($R_1$) from the soil level to the highest curving point in the fruit peduncle.

FIG. 3 shows two photographs of flowering plants representing cvs. 9107 (panel A) and 9001 (panel B). Both mutants are taller than the original 'ADI'. The 9107 is shorter than the 9001. When compared to other Cavendish cvs. all the ADI clones, original and mutants are significantly shorter. Plants were grown in the Western Galilee according to normal growing regimes of irrigation and fertilization in the Western Galilee, Israel. The data represent the average of 1500 clones of each of 9001 (tall genotype) and 9107 (short genotype). The plants were grown in the Western Galilee. Photos were taken approximately 10 weeks post flowering of the second fruit cycle (R1).

FIG. 4 shows average date of flowering of the second cycle of fruit ($R_1$) of a population of 1500 plants per cultivar, approximately 13 months after planting in the field. Plants were grown in the Western Galilee according to normal growing regimes of irrigation and fertilization in the Western Galilee, Israel. The two 'ADI' clones preceded the other Cavendish cvs., but 9001 and 9107 flowered at the same time. The latest cv. to flower was Jaffa as expected.

FIG. 5 shows banana fruit (finger) characteristics. Banana finger length is measured in centimeters (cm) and the weight in grams (gm). The average finger parameters were measured in the second cycle of fruit ($R_1$) of a population of 1500 plants per cultivar, approximately 13 months after planting in the field. Representative fingers were measured. The representative finger being the central finger of the inner whorl of fruit of the second hand from the top. Plants were grown in the Western Galilee according to normal growing regimes of irrigation and fertilization in the Western Galilee, Israel.

It seems from FIG. 5 that all ADI cultivars have longer and heavier fingers in the second hand. This will be reflected in the total yield.

FIG. 6 shows bunch weight in the second cycle of fruit ($R_1$). The weight is measured in Kg. The data represent a population of 1500 plants per cultivar, approximately 13 months at harvest. Plants were grown in the Western Galilee, Israel according to normal growing regimes of irrigation and fertilization in the Western Galilee, Israel.

The data in FIG. 6 show a clear advantage to the 'JAFFA' followed by the shorter ADI clone 9107 and with 'GN' having the lowest weight. In the 9107 the bunches were heavier than the precursor 'ADI' cv. The field experiment was performed in the Western Galilee, Israel, as previously described.

FIG. 7 shows Indexing of Yield calculated with the formula that takes two parameters into account: Kgs of fruit per bunch adequate for export, and the time of flowering. The field experiment was performed in the Western Galilee, Israel, however due to the winter conditions in Israel the plants ceased growing. Thus, we used the cycling time in Martinique to compensate for the retardation of growth in Israel.

This measurement reflects quality and yield of the plants. However, given the Israeli winters we had to assign all the cvs. and the two clones the following timing data, which will be inaccurate for Martinique but will reflect the differences. By far the best performing clone is 9107 as the time to flowering combined with bunch weight exceeds the other 'ADI' cvs. 'JAFFA' exhibited a higher bunch weight but flowering cycle of 'JAFFA' is significantly longer.

CHARACTERISTICS OF THE NEW VARIETY

An apparent distinguishing morphological feature between 'ADI 9107' and its originator 'ADI' is a malformation of the fruit bunch that was prevalent in the precursor cultivar 'ADI' that was improved to be a normal fruit arrangement phenotype in the mutant 9107, FIG. 1. When comparing to 'ADI', the 'ADI 9107' is slightly taller 220 cm compared to 235 cm respectively. The second selection mutant 'ADI 9001' is even taller, 271 cm. Nevertheless, all the 'ADI' cultivars are significantly shorter than 'GAL', 'GN' and 'JAFFA', FIG. 2 and FIG. 3. It is well known to those of ordinary skill in the art that dwarf banana clones of a given variety will have a reduced bunch weight and shorter finger length. In this case 'ADI 9107' plants have a significantly heavier bunch despite the dwarf phenotype FIG. 5. In FIG. 4. the dates of flowering of the second cycle of fruit development; all three 'ADI' cultivars flowered approximately at the same calendar date (April 30$^{th}$). 'ADI' cultivars preceded 'GAL', 'GN', and 'JAFFA' by 10, 15, and 23 days respectively. The weight and length of the representative fingers of the 'ADI 9107' exceed those of the 'ADI 9001' as well as other Cavendish types. The two ADI cultivars (9107 and 9001) had the same number of fingers in the representative hand (second from the top in the bunch) and 2 more fingers than 'GAL', 'GN' and 'JAFFA' FIG. 6. Bunch weight is presented in FIG. 6. The bunch weight of 'ADI 9107' was greater than its originator 'ADI', (7% more), but 'JAFFA' weighed the most. Finally, the total components of yield were calculated in FIG. 7., using the formula that combines bunch weight and cycling time. This indexing formula is widely used in our selection work. 'ADI 9107' received the highest score (139.2) followed by 'ADI 9001' (125.6) and the precursor 'ADI' (118.6). Of the other Cavendish cultivars 'JAFFA' received the highest score (109) and 'GN' the lowest (97.6).

BRIEF SUMMARY OF THE INVENTION

In the present invention we describe a distinct elite 'Cavendish' selection, 'ADI 9107', an improved bunch structure despite having a dwarf-like stature, it has a higher fruit yield, longer and heavier fruit ("fingers") and early flowering similar to the originator cultivar 'ADI' but superior to the other Cavendish cultivars.

DETAILED BOTANICAL DESCRIPTION

Detailed botanical description of the new and distinct selection 'ADI 9107', which includes its general appearance, pseudostem and suckers, petiole, midrib, leaf, inflorescence and male bud, flower bract, male flower, and fruit. This description is based on observations of specimens grown in the Western Galilee, Israel, 14 months after planting. The plantation is at 30 m above sea level, approximately 1200 m East of the Mediterranean Sea, adjacent to the town of Shlomi. The description is based on an observation of approximately 50 plants grown in a commercial plantation. Data was collected in April and May 2017. The descriptors presented herein are in accordance with and include all of the 117 international standards found in "Descriptors for Banana (*Musa* spp.)" elaborated by CIRAD/INIBAP/IPGRI. The color terminology is in accordance with The U.K.'s Royal Horticultural Society's Colour Chart, 2001. Ploidy: Triploid (AAA). Leaf habit: Drooping.

Pseudostem: Height: 2.35 m, measured from the ground to the highest part of the plant at the point where the petiole curves downward. Aspect: The leaves generated faster than the 'ADI 9107' selection. Pseudostem color: Light Green (144-A). Appearance: Dull (waxy). Predominant underlying color of the pseudostem: Light Green (145-A). Pigmentation of the underlying pseudostem: Red-Purple (N59-A). Sap color: Watery. Wax on leaf sheaths: Very waxy. Number of suckers: 7. Position of suckers: Close to parent (vertical growth).

Petiole: Lenticels at petiole base: Approximately 1 cm wide. Lenticel color: Brown (200-B). Petiole canal leaf III: open with margins spreading. Petiole margins: Winged and clasping the pseudostem. Wing type: Dry. Petiole wing color: Grey-brown (199-D). Petiole margin color: Green (143-C). Edge of petiole margin: Very light green-translucent. Petiole margin width: 8 to 13 mm.

Leaf blade: Length: 190-206 cm. Leaf blade width: 64-85 cm. Petiole length: 48-67 cm. Color of leaf upper surface: Green (137-A). Appearance of leaf upper surface: Shiny. Color of leaf lower surface: Green (137-B). Appearance of leaf lower surface: Dull. Wax on leaves: Moderately waxy. Insertion point of leaf blades on petiole: Symmetrical. Shape of leaf blade base: Tapered in first leaves going to both rounded in later leaves. Leaf corrugation: Few stripes. Color of midrib dorsal surface: Green (138-B). Color of midrib ventral surface: Yellow-Green (146-D). Color of cigar leaf dorsal surface: Green (143-A) Lenticels on leaves of water suckers: No lenticels. Venation pattern: parallel venation in the leaf lamina in the pinnate style. Leaf Shape: Oblong with rounded ends.

Inflorescence/male bud: Peduncle length: 67-72 cm. Empty nodes on peduncle: Two or more. Peduncle width: 6.5-7.5 cm. Peduncle color: Yellow-green (144-A). Peduncle hairiness: Hairless.

Rachis: Present. Position: Falling vertically. Male bud shape: Ovoid. Male bud size: 21-28 cm. Average diameter of male bud: 17 cm.

Bract: Bract base size: Average 12 cm. for the part connected to the rachis. Bract apex shape: Obtuse. Bract length: Average 29 cm. at longest point. Bract width: Average 23 cm. at the widest point. Color of the bract external face: Red-purple (59-A). Color of the bract internal face: Grayed-orange (176-A). Color stripes on bract: With discolored lines on the external face. Bract scars on rachis: Not prominent. Male bract shape: Ovate. Wax on the bract: Moderately waxy. Presence of grooves on the bract: Moderate.

Male flower: Data taken at completion of flower emergence. Male flower behavior: Falling before the bract. Compound tepal basic color: Red-purple (65-A), later becoming grey and black. Lobe color of compound tepal: Yellow (8-A). Free tepal appearance: Corrugated. Style shape: Straight. Stigma color: Orange (25-C). Ovary basic color: Yellow (8-D). Ovary pigmentation: Very few signs of pigmentation.

Fruit position: Curved upward. Apex: somewhat rounded. Number of fruit per hand: 19 average. Fruit length: 20.4 cm. (when counting 8 hands from the top down). Fruit shape longitudinal curvature: Slightly curved. Fruit circumference: 15.2 cm. average. Fruit pedicel length: 3.8 cm. average. Pedicel surface: Hairless. Immature fruit peel color: Green (144-A). Mature fruit peel color: Yellow (14-C). Fruit peel thickness: 2.0 mm. Adherence of the fruit peel: Fruit peels easily. Cracks in fruit peel: Without cracks. Pulp in fruit: With pulp. Pulp color before maturity: White (155-D). Pulp color at maturity: (155-D). Fruit is eaten: Ripe. Flesh texture: Firm. Predominant taste: Sweet. Main use: Dessert banana. Presence of seed: No seeds.

Agronomic characteristics: Averages taken during 2016-2017 for second crop in a plot of 1900 plants per hectare:

Number of leaves at flowering: 14. Average bunch weight 51.01 kg. Number of marketable (fruit that exceed the length of 17 cm) hands: 9. Finger length: Average 20.4 cm. Average number of fingers per hand: 18.6.

DESCRIPTIVE MORPHOLOGICAL CHARACTERISTICS

TABLE 1

| | 9107 | | 9001 | | "ADI" | |
|---|---|---|---|---|---|---|
| Cultivar | Average | ± Std Err. | Average | ± Std Err. | Average | ± Std Err. |
| Number of above ground suckers | 5.6 | 1.17 | 6.4 | 0.4 | 6.1 | 0.6 |
| Pseudostem Diameter 1 m above ground (in cm) | 20.2 | 0.97 | 19.4 | 0.24 | 19.4 | 0.3 |
| Spots are present or absent on the pseudostem | absent | | absent | | absent | |
| Petiole length | 35.6 | 1.69 | 24 | 1.84 | 32.2 | 2.2 |
| Peduncle length | 56 | 6.78 | 77.6 | 8.32 | 65.3 | 7.2 |
| Peduncle diameter | 7.6 | 0.51 | 9 | 0.55 | 7.8 | 0.52 |
| Length of the bunch | 72 | 5.61 | 71 | 5.34 | 71 | 5.34 |
| Diameter of the bunch | 37.8 | 1.3 | 34.6 | 0.4 | 33.8 | 0.3 |
| Number of fruit per hand | 19 | 0.45 | 20 | 0.71 | 19.2 | 0.5 |

Botanical Description of 2 new cultivars derived from the original 'ADI'. The data were collected from a commercial plantation of different ADI cultivars grown in the Western Galilee Israel. Each Figure is the average of 30 trees ± Std Err.

Table 1 reveals the number of the above ground suckers do not differ greatly between the different cultivars. Cultivar 9107 produced 5.6 suckers compared to 6.4 for 9001 and 6.1 for 'ADI'. There are no significant differences in the diameter of the pseudostem for the 3 cultivars (9107, 9001, and 'ADI'). The length of the petiole of 9107 is significantly greater than the other 2 cultivars and on the contrary the peduncle diameter of 9107 is shorter than both other cultivars. The length of the bunch is similar in all 3 cultivars, but the diameter of the bunch is greater in 9107 (37.8, 34.6, 33.8) respectively for 9107, 9001, and 'ADI'. Finally, the total number of fruit per hand counting all marketable hands are 19 for 9107, 20 for 9001, and 19.2 for 'ADI'. Therefore, we conclude that the higher weight in 9107 stems from the size of the fingers rather the number of fingers. This conclusion is supported by the fact that the diameter of the bunch is greater in 9107 compared to the other 2 cultivars.

All 3 cultivars show a drooping growth style compared to other Cavendish types. No pubescence was noticed in any of the 3 cultivars (9107, 9001, and 'ADI').

It is claimed:

1. 'ADI 9107', a new and distinct selection of banana plant, substantially as illustrated and described, which is a dwarf stature plant compared to the other Cavendish cultivars 'GAL', 'GN', 'JAFFA' and 'ADI 9001', has higher fruit yield and index of yield compared to its originator 'ADI' and sibling 'ADI 9001', longer fruit ("fingers") and none of the hands on the bunch show malformation, the number of above ground suckers is lower than the 9001 and 'ADI', and the petiole length of 9107 is greater than 9001 and 'ADI', the peduncle length is shorter than 9001 and 'ADI', the peduncle diameter is smaller than 9001, and 'ADI', the length of the bunch is similar to 9001 and 'ADI', the diameter of the bunch is greater than 9001, and 'ADI' and the number of fruit per hand is similar to 9001 and 'ADI'.

* * * * *

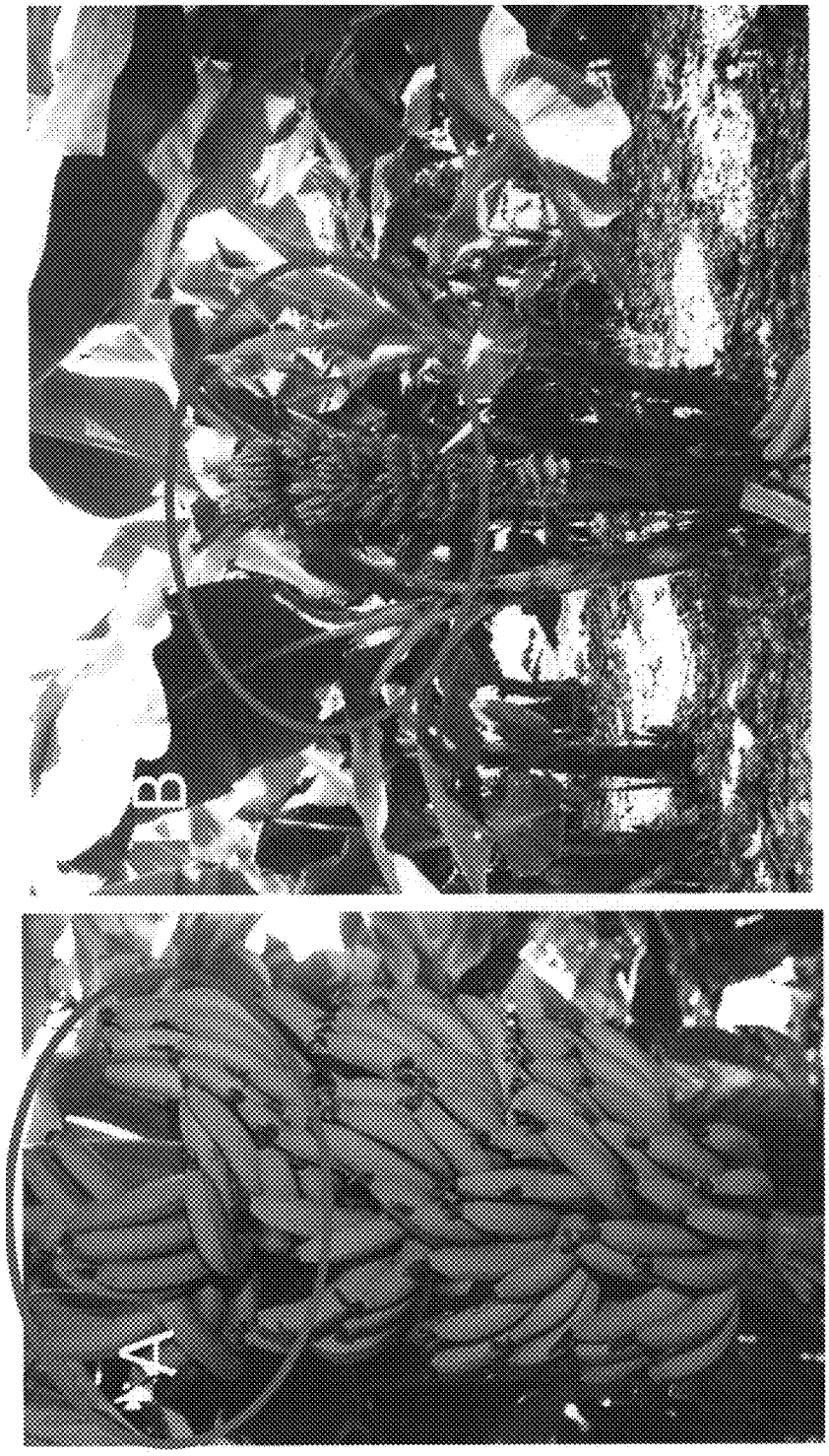
Figure 1 : Bunch Structure Comparison

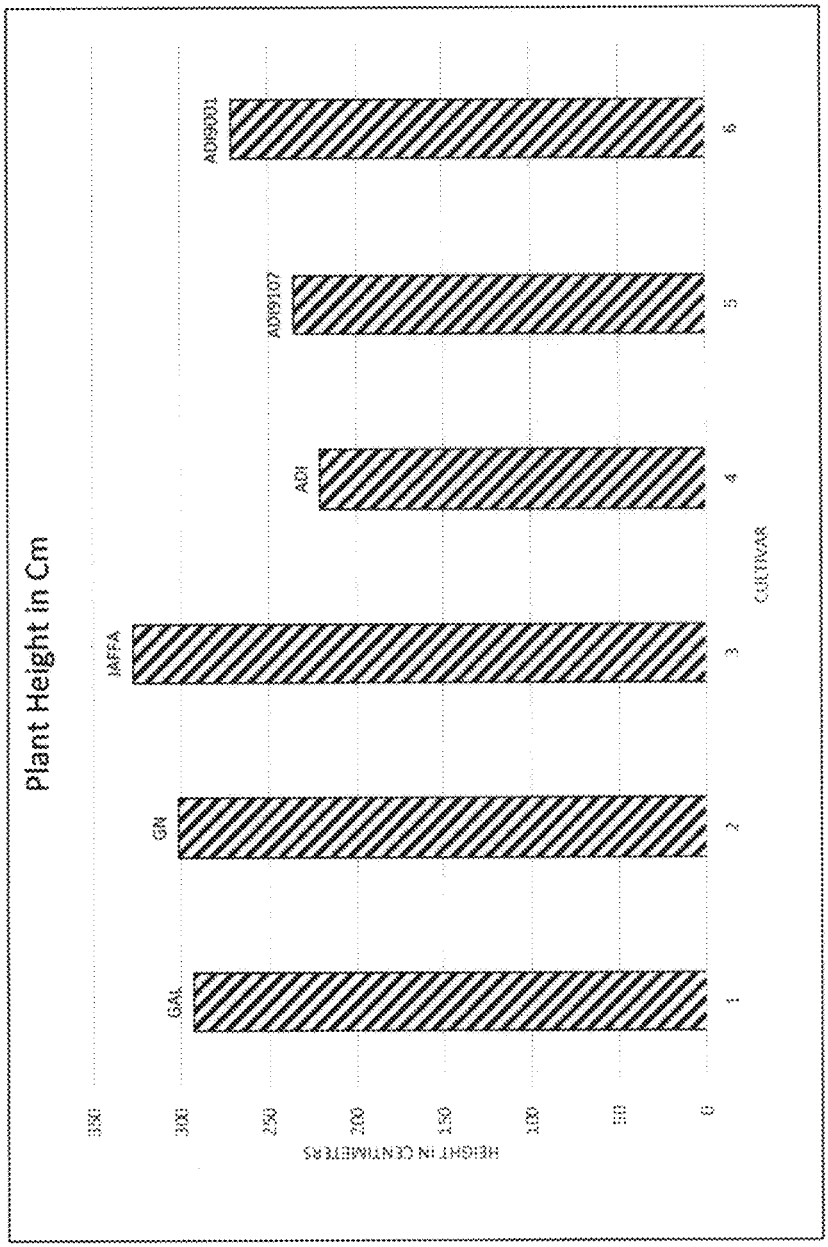
| | |
|---|---|
| GAL | 293 (±28) |
| GN | 301 (±32) |
| JAFFA | 327 (±20) |
| ADI | 220 |
| ADI 9107 | 235 (±19) |
| ADI 9001 | 271 (±29) |
Figure 2 : Plant Height

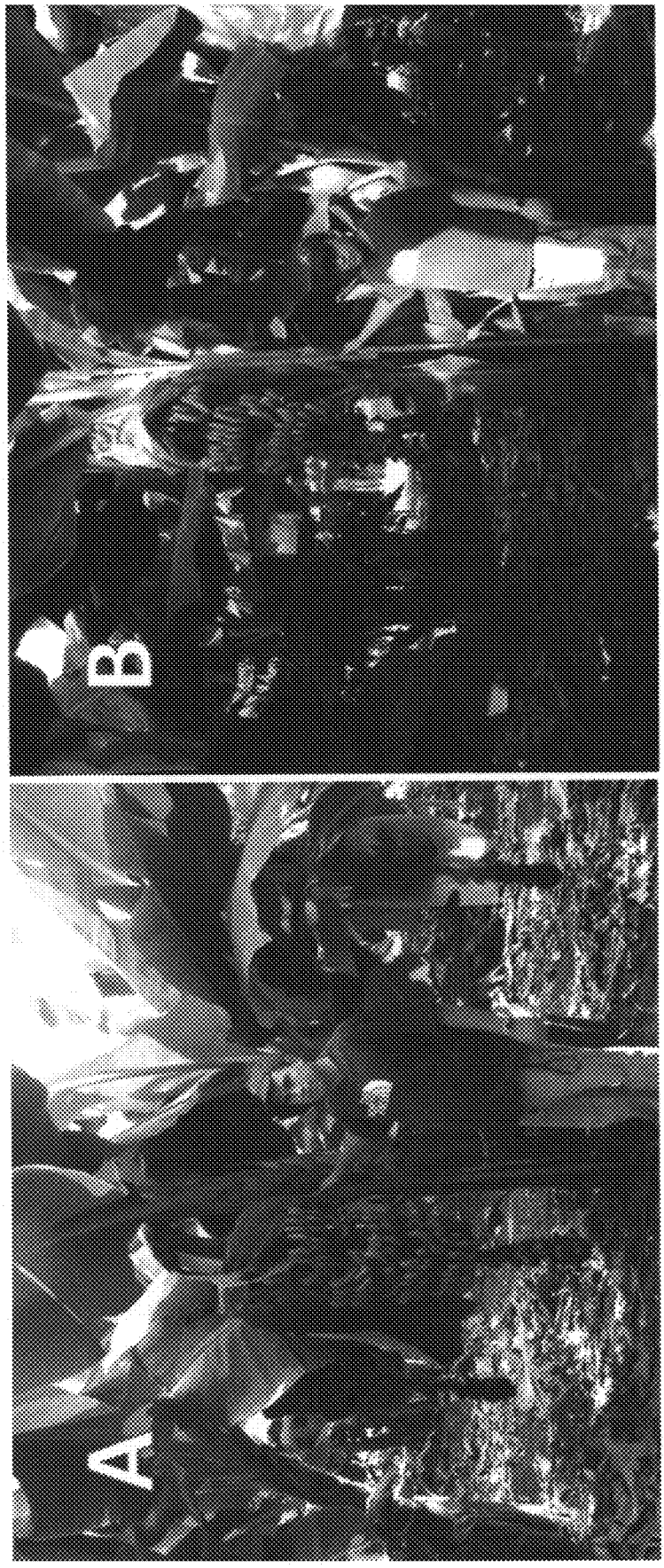
Figure 3 : Photo Plant Height Comparison

| CV or clone | Average time of flowering |
|---|---|
| GAL | May 10 |
| GN | May 15 |
| JAFFA | May 23 |
| 'ADI' | April 30 |
| ADI 9001 | April 30 |
| ADI 9107 | April 30 |

Figure 4: Average Time of Flowering

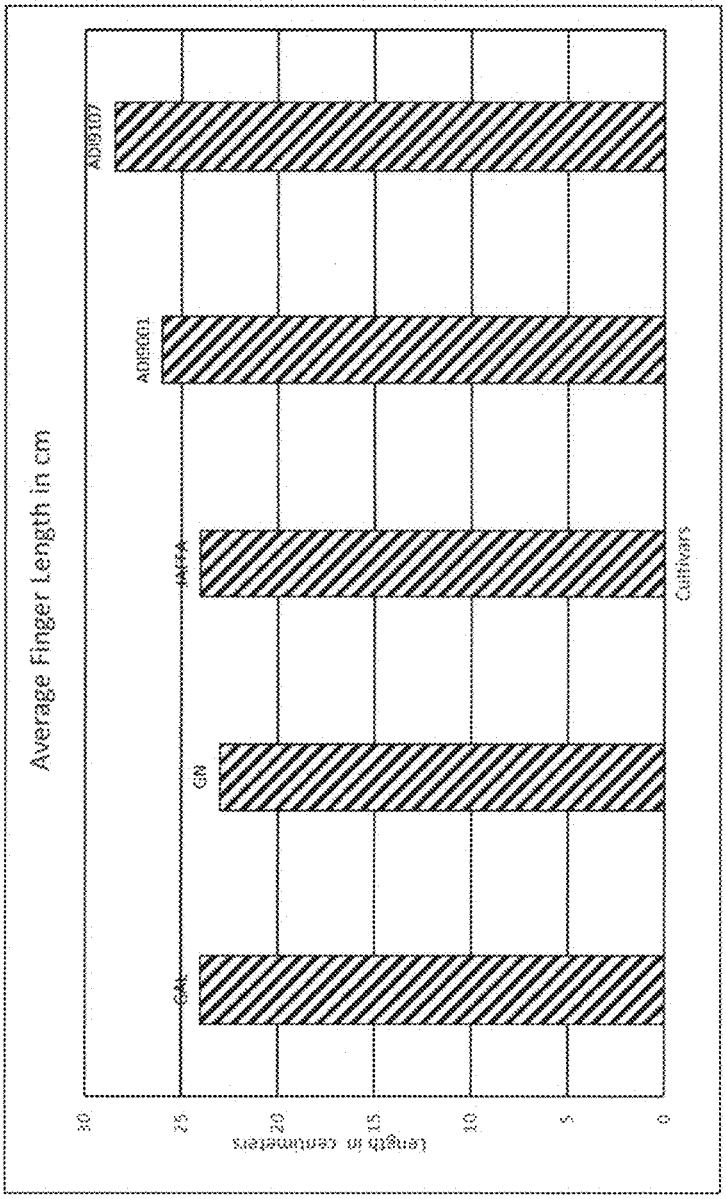
Figure 5A: Finger Length
| Cultivar | Average finger length (cm) in second hand middle finger |
|---|---|
| GAL | 24.0 |
| GN | 23.0 |
| JAFFA | 24.0 |
| ADI 9001 | 26.0 |
| ADI 9107 | 28.5 |

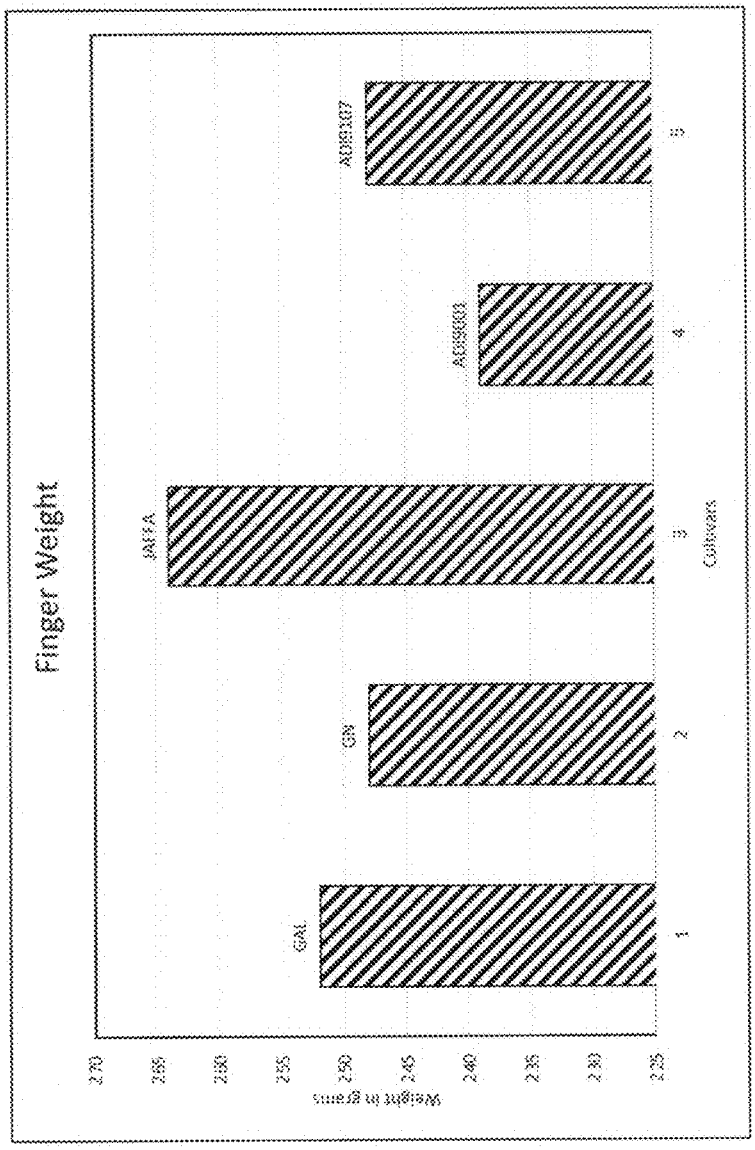
Figure 5B: Finger Weight
| Cultivar | Average finger weight (gm) in second hand middle finger |
|---|---|
| GAL | 252 |
| GN | 248 |
| JAFFA | 264 |
| ADI 9001 | 239 |
| ADI 9107 | 248 |

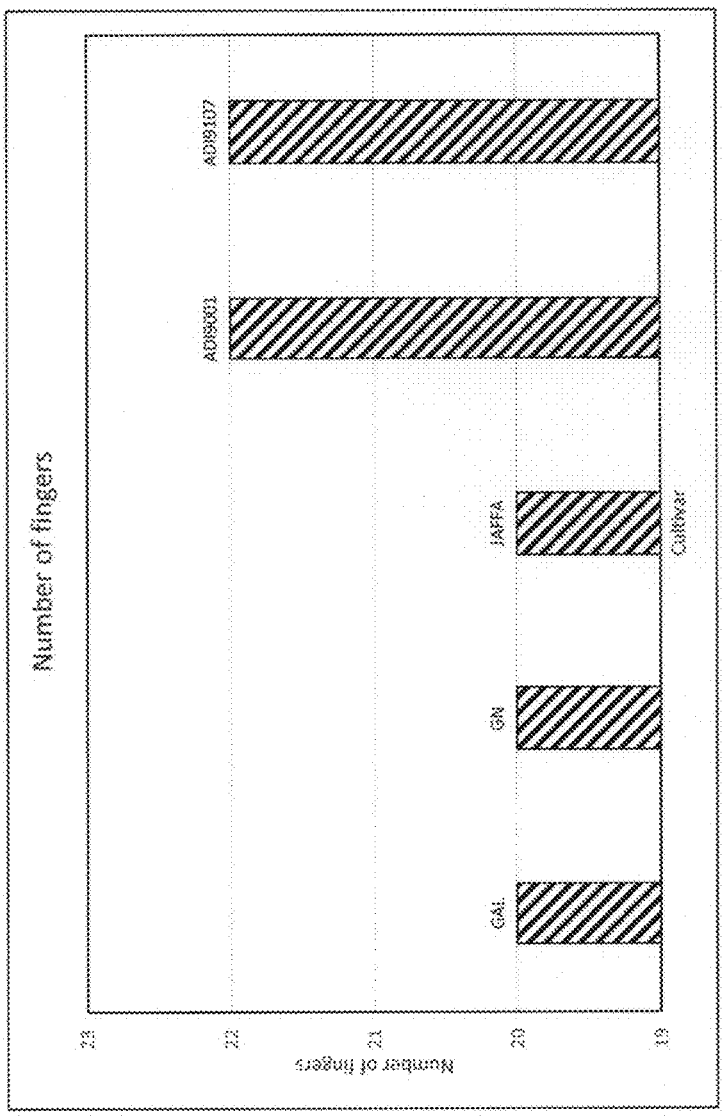
Figure 5C: Number of Fingers in the Second Hand
| | Number of fingers per second hand from the top of the bunch |
|---|---|
| GAL | 20 |
| GN | 20 |
| JAFFA | 20 |
| AD19001 | 22 |
| AD19107 | 22 |

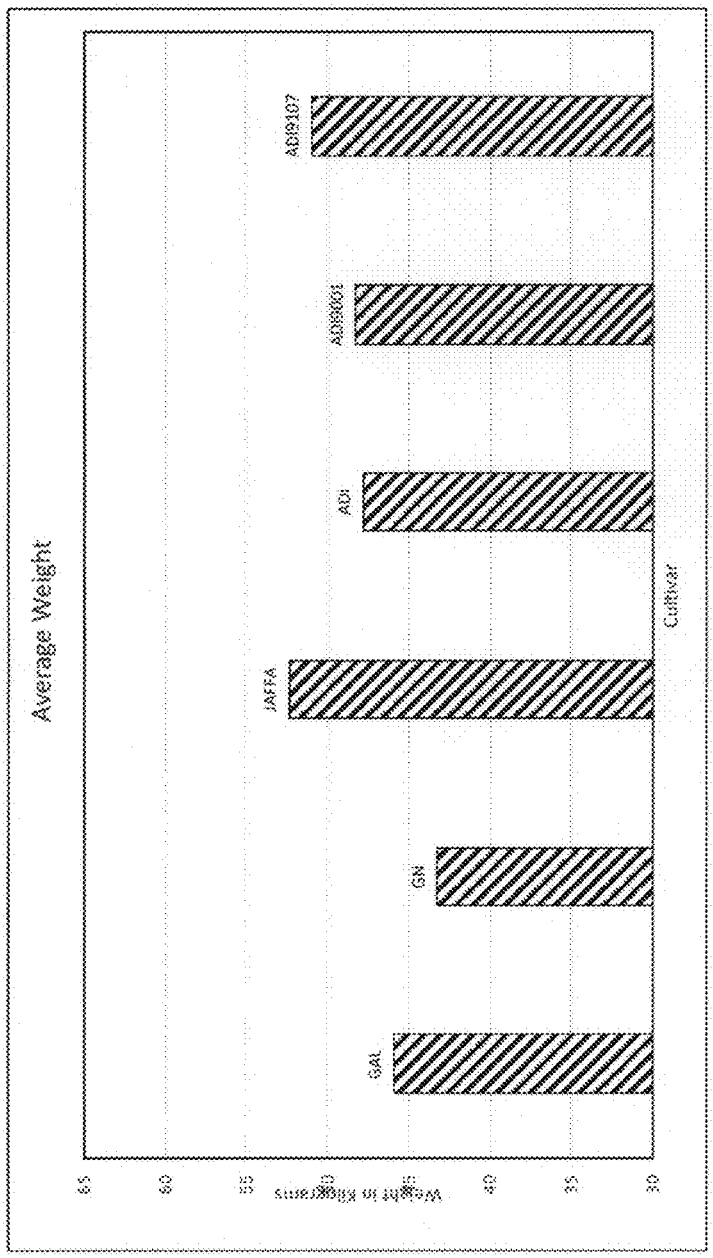
Figure 6: Bunch Weight
| Cultivar | Weight in Kilograms | Average bunch weight (± Standard deviation) |
|---|---|---|
| GAL | 45.91 | 45.91(±3) |
| GN | 43.26 | 43.26 (±12) |
| JAFFA | 52.40 | 52.40 (±3.3) |
| ADI | 47.82 | 47.82 (±4.1) |
| ADI 9001 | 48.30 | 48.3 (±3.0) |
| ADI 9107 | 51.01 | 51.01 (±4.2) |
| | | |

| Cultivar | 52/Weeks to flowering (time of flowering was measured in Martinique) | Bunch weights in first + second flush $(W_0 + W_1)/2$ | Indexing according to the formula $(YI) = W_0 + W_1 X (52/(F_0 to F_1))$ |
|---|---|---|---|
| GAL | 2.36 | 45.91(±3) | 108.3 |
| GN | 2.26 | 43.26 (±12) | 97.76 |
| JAFFA | 2.08 | 52.40 (±3.3) | 109.0 |
| ADI | 2.48 | 47.82 (±4.1) | 118.6 |
| ADI 9001 | 2.6 | 48.3 (±3.0) | 125.6 |
| ADI 9107 | 2.73 | 51.01 (±4.2) | 139.2 |

Figure 7: Indexing of Yield